(12) United States Patent
Baudino et al.

(10) Patent No.: US 7,442,183 B2
(45) Date of Patent: *Oct. 28, 2008

(54) TECHNIQUES FOR SELECTIVE ACTIVATION OF NEURONS IN THE BRAIN, SPINAL CORD PARENCHYMA OR PERIPHERAL NERVE

(75) Inventors: Michael Baudino, Minneapolis, MN (US); Mark T. Rise, Monticello, MN (US)

(73) Assignee: Medtronic, Inc., Minneapolis, MN (US)

( * ) Notice: Subject to any disclaimer, the term of this patent is extended or adjusted under 35 U.S.C. 154(b) by 455 days.

This patent is subject to a terminal disclaimer.

(21) Appl. No.: 10/053,329

(22) Filed: Nov. 9, 2001

(65) Prior Publication Data
US 2002/0062143 A1    May 23, 2002

Related U.S. Application Data

(63) Continuation of application No. 09/302,519, filed on Apr. 30, 1999, now Pat. No. 6,353,762.

(51) Int. Cl.
*A61M 31/00* (2006.01)
(52) U.S. Cl. .................. 604/93.01; 604/67
(58) Field of Classification Search ........... 604/890.1, 604/891.1, 892.1, 93.01, 65–67, 164.01, 604/164.08, 131, 288.01–288.04; 128/DIG. 12
See application file for complete search history.

(56) References Cited

U.S. PATENT DOCUMENTS

| | | |
|---|---|---|
| 3,347,224 A | 10/1967 | Adams |
| 3,361,848 A | 1/1968 | Muller |
| 3,665,916 A | 5/1972 | Kobayashi et al. |
| 3,754,555 A | 8/1973 | Schmitt |
| 4,136,701 A | 1/1979 | Barton et al. |
| 4,357,946 A | 11/1982 | Dutcher et al. |
| 4,522,212 A | 6/1985 | Gelinas et al. |

(Continued)

FOREIGN PATENT DOCUMENTS

EP    0479435    4/1992

(Continued)

OTHER PUBLICATIONS

T. Riechert, H. Spuler, "*Instrumentation of Stereotxy*," Stereotaxy of the Human Brain, (1982) pp. 350-363, 606, 639.

*Primary Examiner*—Kevin C. Slrmons
*Assistant Examiner*—Catherine N Witczak

(57) ABSTRACT

Techniques capable of selectively affecting and adjusting a volume of neural tissue in the brain, parenchyma of the spinal cord, or a peripheral nerve are disclosed. A lumen having at least one opening at its distal end that is capable of directing a lead outwardly along a predetermined trajectory is preferred. The lumen is capable of accepting a plurality of leads that can project outward in different directions from the distal end of the lumen. The leads have one or more electrodes at its ends and are thereby configured by the lumen in accordance with a predetermined two- or three-dimensional geometry. Anode/cathode relationships may be established between the electrodes by the operator to stimulate the neural tissue surrounding these electrodes. The operator may also adjust the stimulation to selectively stimulate the desired portion of the brain, spinal cord, peripheral nerve. Sensor feedback may be implemented to adjust the treatment therapy.

25 Claims, 19 Drawing Sheets

U.S. PATENT DOCUMENTS

| | | | |
|---|---|---|---|
| 4,533,346 A * | 8/1985 | Cosgrove et al. | 604/66 |
| 4,692,147 A | 9/1987 | Duggan | |
| 5,113,859 A | 5/1992 | Funke | |
| 5,236,424 A | 8/1993 | Imran | |
| 5,259,387 A | 11/1993 | dePinto | |
| 5,282,845 A | 2/1994 | Bush et al. | |
| 5,314,462 A | 5/1994 | Heil, Jr. et al. | |
| 5,354,279 A * | 10/1994 | Hofling | 604/164.12 |
| 5,476,498 A | 12/1995 | Ayers | |
| 5,514,174 A | 5/1996 | Heil, Jr. et al. | |
| 5,551,426 A | 9/1996 | Hummel et al. | |
| 5,588,960 A * | 12/1996 | Edwards et al. | 604/20 |
| 5,609,623 A | 3/1997 | Lindegren | |
| 5,685,839 A | 11/1997 | Edwards et al. | |
| 5,711,316 A * | 1/1998 | Elsberry et al. | 128/898 |
| 5,713,922 A | 2/1998 | King | |
| 5,722,402 A | 3/1998 | Swanson et al. | |
| 5,725,525 A | 3/1998 | Kordis | |
| 5,792,186 A | 8/1998 | Rise | |
| 5,925,070 A | 7/1999 | King et al. | |
| 5,964,796 A * | 10/1999 | Imran | 607/122 |
| RE36,386 E * | 11/1999 | Abbott et al. | 604/6.13 |
| 6,038,472 A | 3/2000 | Williams et al. | |
| 6,094,596 A | 7/2000 | Morgan | |
| 6,094,598 A | 7/2000 | Elsberry et al. | |
| 6,129,685 A * | 10/2000 | Howard, III | 600/585 |
| 6,353,762 B1 * | 3/2002 | Baudino et al. | 607/45 |
| 6,385,472 B1 | 5/2002 | Hall et al. | |
| 6,425,887 B1 * | 7/2002 | McGuckin et al. | 604/272 |
| 2003/0069541 A1 * | 4/2003 | Gillis et al. | 604/164.01 |

FOREIGN PATENT DOCUMENTS

| | | |
|---|---|---|
| EP | 0965359 | 12/1999 |
| WO | PCT/US95/00906 | 7/1995 |
| WO | WO 96/10961 | 4/1996 |
| WO | WO 97/39797 A1 | 10/1997 |
| WO | WO 98/48887 | 11/1998 |
| WO | WO 99/00067 A1 | 1/1999 |

* cited by examiner

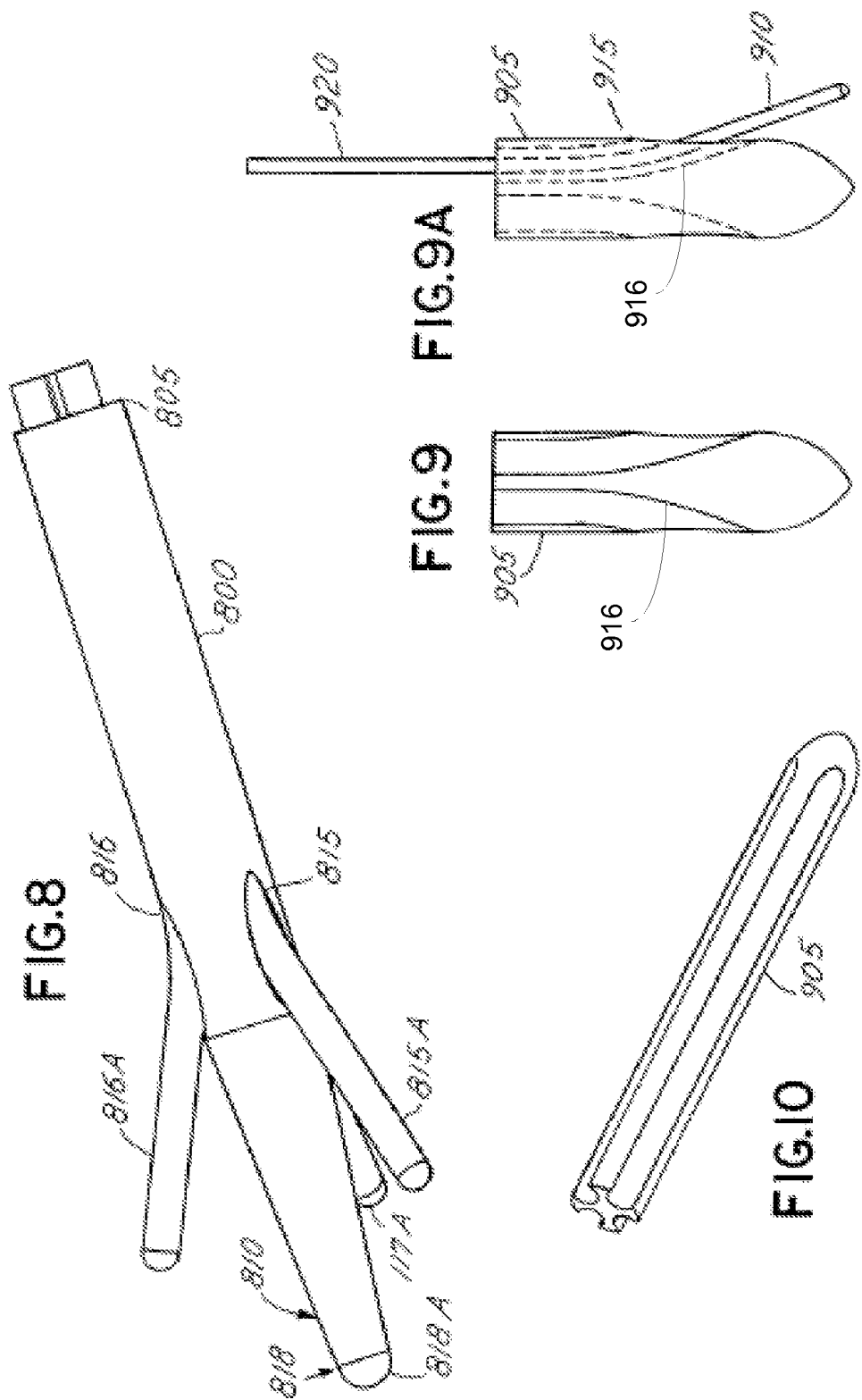

TECHNIQUES FOR SELECTIVE ACTIVATION OF NEURONS IN THE BRAIN, SPINAL CORD PARENCHYMA OR PERIPHERAL NERVE

This patent application is a continuation of U.S. patent application Ser. No. 09/302,519, filed Apr. 30, 1999, for which priority is claimed. This parent application is incorporated herein by reference in its entirety.

BACKGROUND OF THE INVENTION

1. Field of the Invention

The present Invention relates to techniques for providing treatment therapy to neural tissue, and more particularly relates to techniques for selectively delivering treatment therapy to neural tissue located within a volume of the brain, spinal cord, or peripheral nerve.

2. Description of Related Art

Electrical stimulation techniques have become increasingly popular for treatment of pain and various neurological disorders. Typically, an electrical lead having one or more electrodes is implanted near a specific site in the brain or spinal cord of a patient. The lead is coupled to a signal generator which delivers electrical energy delivered through the electrodes creates an electrical field causing excitation of the nearby neurons directly or indirectly treat the pain or neurological disorder.

Presently, only highly skilled and experiences practitioners are able to position a stimulation lead in such a way that the desired volume of brain tissue is influences and desired results are obtained over time with minimal side effects. It requires much time and effort to focus the stimulation on the population of nerve cells subserving the appropriate function in the desired body region during surgery. These leads cannt be moved by the physician without requiring a second surgery.

A major practical problem with these systems is that the response of the nervous system may change in time. For example, when treating pain even if paresthesia covers the area in pain perfectly during surgery, the required paresthesia pattern often changes later due to lead migration, histological changes (such as the growth of connective tissue around the stimulation electrode), neural plasticity or disease progression. As a result, the electrical energy is directed to stimulate undesired portions of the brain or spinal cord. Redirecting paresthesia without requiring a second surgery is therefore highly desirable. With present single channel, linear electrode array approaches, however, it is difficult to redirect stimulation effects afterwards, even though limited readjustments can be made by selecting a different contact combination, pulse rate, pulse width or voltage. These problems are found not only with spinal cord stimulation (SCS), but also with peripheral nerve stimulation (PNS), depth brain stimulation (DBS), cortical stimulation and also muscle or cardiac stimulation.

In the case of DBS where an electrical lead is implanted within the brain, it is particularly critical that the lead be properly positioned. If the lead is not properly positioned and needs to be moved, it must be removed and re-inserted thereby increasing the risk of bleeding and damage to the neuropile. It is therefore desirable to place the lead within the brain in one attempt and avoid subsequent movement or repositioning of the lead.

Recent advances in this technology have allowed the treating physician or the patient to steer the electrical energy delivered by the electrode once it has been implanted within the patient. For example, U.S. Pat. No. 5,713,922 entitled "Techniques for Adjusting the Locus of Excitation of Neural Tissue in the Spinal Cord or Brain," issued on Feb. 3, 1998 to and assigned to Medtronic, Inc. discloses one such example of a system for steering electrical energy. Other techniques are disclosed in application Ser. No. 08/814,432 (filed Mar. 10, 1997) and Ser. No. 09/024,162 (filed Feb. 17, 1998). Changing the electric field distribution changes the distribution of neurons recruited during a stimulus output thus provides the treating physician or the patient the opportunity to alter the physiological response to the stimulation. The steerability of the electric field allows the user to selectively activate different groups of nerve cells without physically moving the electrode.

These steering techniques, however, are limited to primarily two-dimensional steering since the electrodes are positioned in a linear or planar configuration. In the case of deep brain stimulation (DBS), the stimulation treatment requires stimulation of a volume of neural tissue. Since the exact location of the desired tissue is unknown, it is desirable to steer the electrical field in more than just two-dimensional space.

Another problem with DBS is that the insertion of electrical leads within the brain presents risks of bleeding or damage to the brain tissue. Where multiple leads are inserted within the brain, this risk also multiplies. Often during placement of a lead within the brain, the lead is not placed in the desired location. The lead must be removed and re-inserted into the brain. Each re-insertion of the lead poses additional risk of injury.

Accordingly, there remains a need in the art to provide a two- or three-dimensional steerable electrical stimulation device that may be implanted within the brain or spinal cord parenchyma that requires minimal adjustment of the lead position.

SUMMARY OF THE INVENTION

As explained in more detail below, the present invention overcomes the above-noted and other shortcomings of prior techniques for electrical stimulation of the brain, spinal cord parenchyma and peripheral nerve. The present invention provides a technique for insertion of electrode leads that require minimal adjustment once the lead has been inserted. Additionally, the present invention enables the user to selectively stimulate neurons or neural tissue within a specific volume of tissue. In a preferred embodiment, the present invention includes a cannula, a plurality of leads, and at least one therapy delivery element or electrode at the distal ends of each of the leads. The cannula has a lumen and at least two openings at its distal end. The leads may be inserted into the cannula's lumen and projected outward at the distal end from each of the openings along a predetermined trajectory. A therapy delivery device, such as a signal generator, is coupled to one or more therapy delivery elements, such as electrodes. The signal generator is capable of selectively providing electrical energy via the electrode to create an electrical field. The system may selectively adjust the electrical field created by the electrical energy. Optionally, a sensor may be included for generating a signal related to the extent of a physical condition for treating a neurological disorder or pain. The sensor signal may then be used to adjust at least one parameter of the electrical energy provided to the electrode.

In another embodiment, the present invention is implemented within a drug delivery system. In such a case, the therapy delivery device may be a pump and the therapy delivery element is a catheter. Alternatively, both electrical stimulation and drug delivery may be implemented.

By using the foregoing techniques, electrical stimulation and/or drug delivery may be adjusted and/or steered to a precise target within a volume of neural tissue to provide the desired treatment therapy. Further, the present invention provides a method of lead placement that allows the surgeon to explore a larger volume of brain tissue using only a single pass of the lead introducer into the brain which will reduce the inherent risk of surgery. Examples of the more important features of this invention have been broadly outlined above so that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 8 is an illustration of a cannula in accordance with a preferred embodiment of the present invention;

FIGS. 9 and 9A are cross sectional views of a cannula in accordance with another embodiment of the invention;

FIG. 10 is an illustration of a guiding mechanism to be inserted within a cannula for directing the trajectory of the electrical leads of the present invention;

DESCRIPTION OF THE PREFERRED EMBODIMENTS

Figure 1:
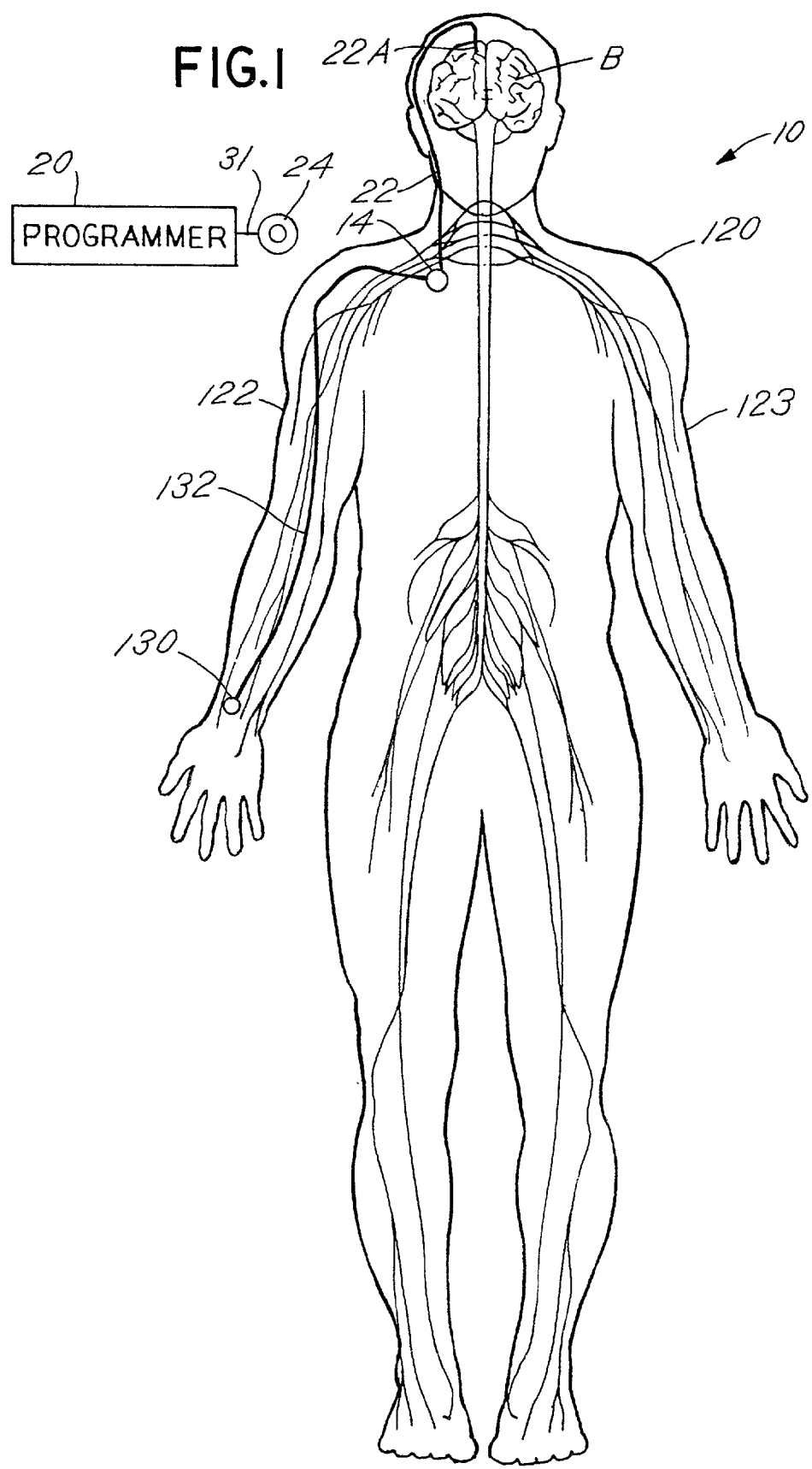
FIG. 1 is a schematic view of a patient having an implant of a neurological stimulation system employing a preferred form of the present invention to stimulate the subthalamic nucleus of the patient.
Figure 2:
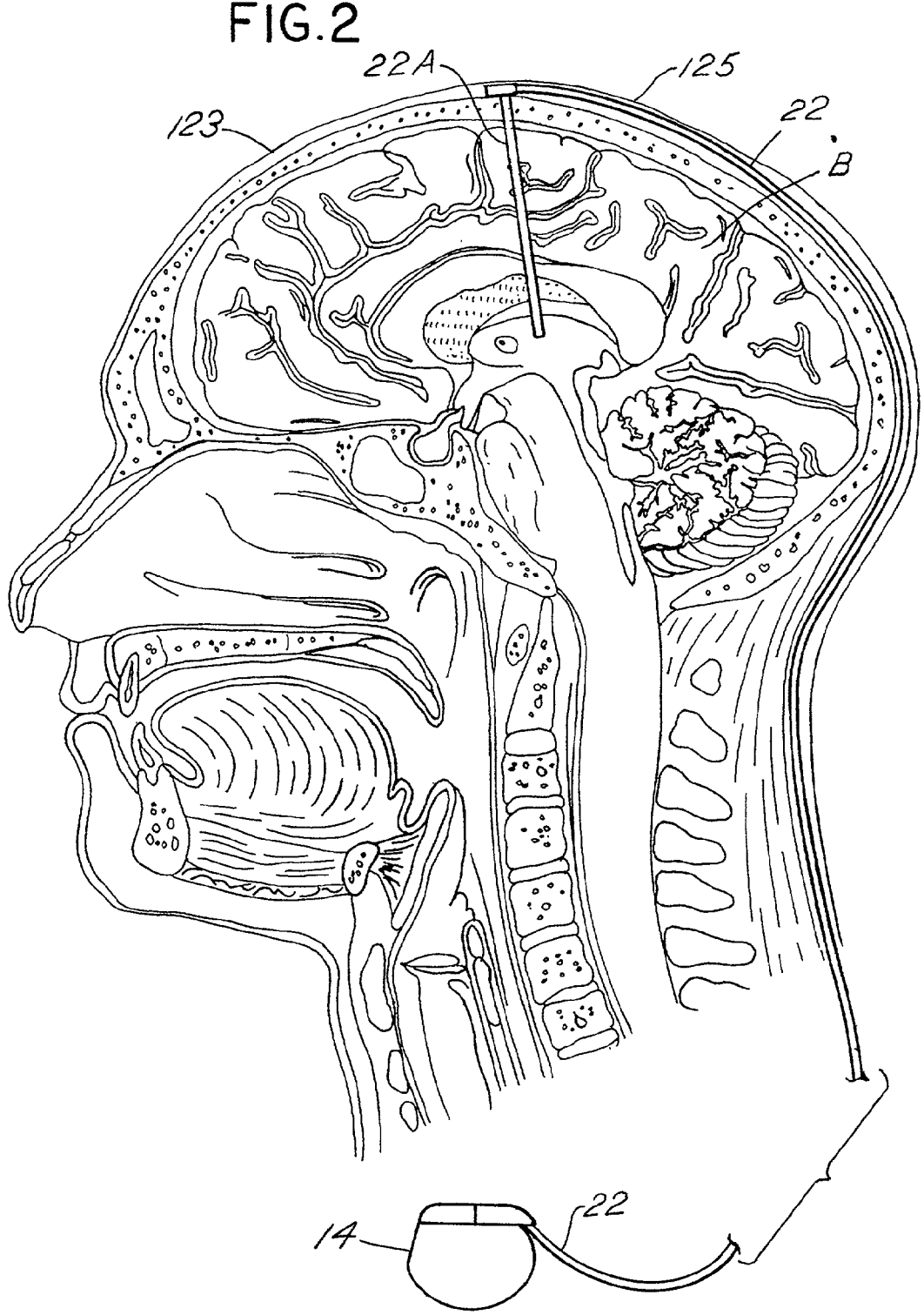
FIG. 2 is a cross sectional view of brain B showing implantation of a cannula within the brain.
Figure 3:
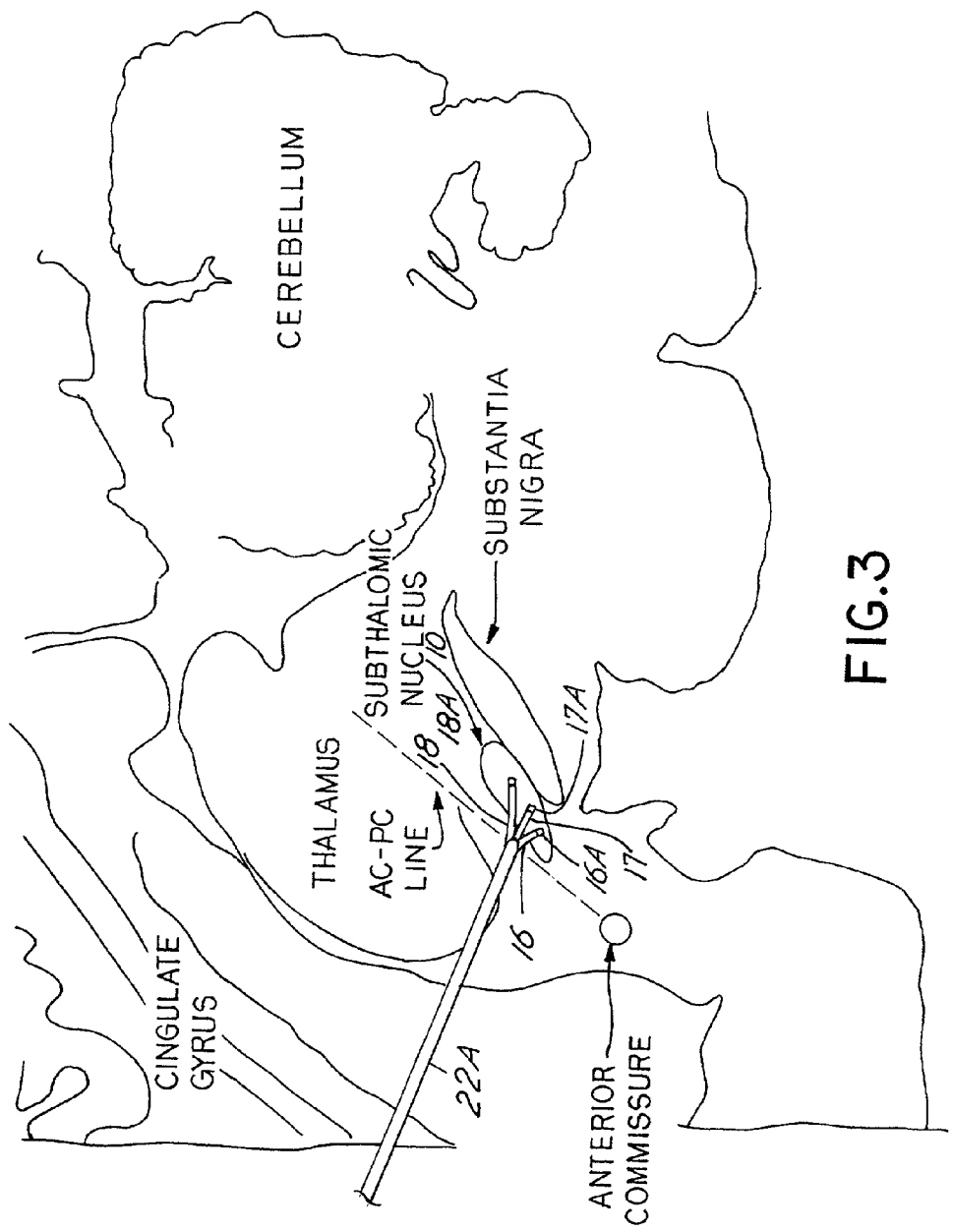
FIG. 3 is a sagittal view of a subthalamic nucleus showing implantation of electrical leads having electrodes at the distal ends.

FIG. 1 is a schematic view of a patient 10 having an implant of a neurological stimulation system employing a preferred form of the present invention to stimulate the subthalamic nucleus of the patient. The preferred system employs an implantable therapy delivery device or a pulse generator 14 to produce a number of independent stimulation pulses which are sent to a region of the brain parenchyma such as the subthalamic nucleus by insulated leads coupled to therapy delivery devices or electrodes 16A-18A (FIG. 3). Each lead is inserted within cannula 22A. Alternatively, two or more electrodes 16A-18A may be attached to separate conductors included within a single lead. FIG. 2 is a cross section of brain B showing implantation of cannula 22A within the brain. The specific locations within the brain are discussed in further detail herein.

Device 14 is implanted in a human body 120 in the location shown in FIG. 1. Body 120 includes arms 122 and 123. Alternatively, device 14 may be implanted in the abdomen or any other part of the body.

Implantable pulse generator 14 is preferably a modified implantable pulse generator available from Medtronic, Inc. under the trademark ITREL II with provisions for multiple pulses occurring either simultaneously or with one pulse shifted in time with respect to the other, and having independently varying amplitudes and pulse widths. This preferred system employs a programmer 20 which is coupled via a conductor 31 to a telemetry antenna 24. The system permits attending medical personnel to select the various pulse output options after implant using telemetry communications. While the preferred system employs fully implanted elements, systems employing partially implanted generators and radio-frequency coupling may also be used in the practice of the present invention (e.g., similar to products sold by Medtronic, Inc. under the trademarks X-trel and Mattrix).

FIG. 3 is a sagittal view of the subthalamic nucleus 10 of brain B at approximately 11 mm lateral to the midline. The distal ends of insulated leads 16-18 within cannula 22A terminate in electrodes 16A-18A. The electrodes may be conventional DBS™ electrodes, such as model 3387 sold by Medtronic, Inc. Alternatively, electrodes 16A-18A may be constructed like electrical contacts 56, 58 and 60 shown in PCT International Publication No. WO 95/19804, entitled "Multichannel Apparatus for Epidural Spinal Cord Stimulation" (Holsheimer et al., filed 24 Jan. 1994, published 27 Jul. 1995) which is incorporated by reference in its entirety. Electrodes 16A-18A are positioned in a two- or three-dimensional predetermined geometric configuration as described in further detail herein such that they are distributed throughout various portions of a volume of brain parenchyma such as the subthalamic nucleus. An anode/cathode relationship is established between electrodes 16A-18A in the manner described in PCT Publication No. WO 95/19804. For example, electrodes 16A and 18A may be established as anodes (+) and electrode 17A may be established as a cathode (−). The physician or patient may configure the system to utilize any combination of electrodes 16A-18A to selectively establish a locus of action potentials.

Pulses may then be applied to specific electrodes as taught in the PCT Publication No. WO 95/19804 to direct a locus of action potentials in the brain. Pulses in electrodes 16A-18A create a locus of excitation of nerve cells. As preferred, the electrical pulses are independently adjustable within each electrode such that the locus of excitation may be adjusted to deliver the desired therapy. For example, the pulses may overlap in time and may be independently variable in amplitude to best control the areas of activation, or they may also have independently variable pulse widths.

Figure 4:
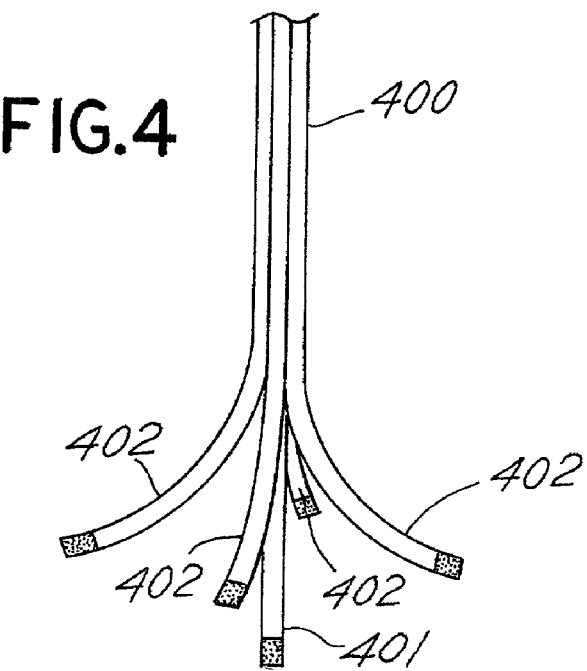
FIGS. 4-7 are exemplary illustrations of various electrical lead configurations capable of selectively stimulating a volume of neural tissue in accordance with the present invention.
Figure 4A:
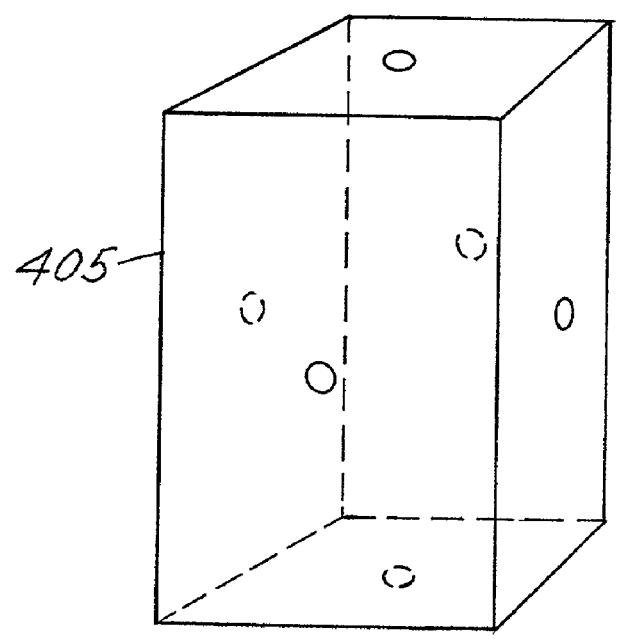
Figure 5:
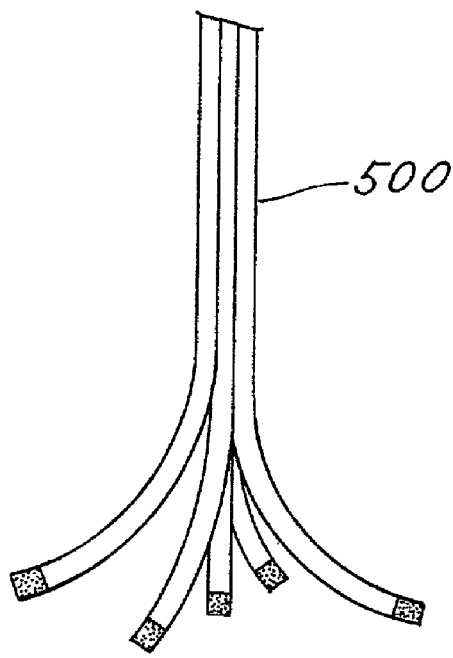
Figure 5A:
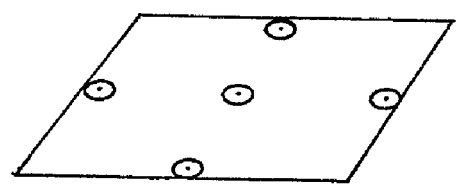
Figure 6:
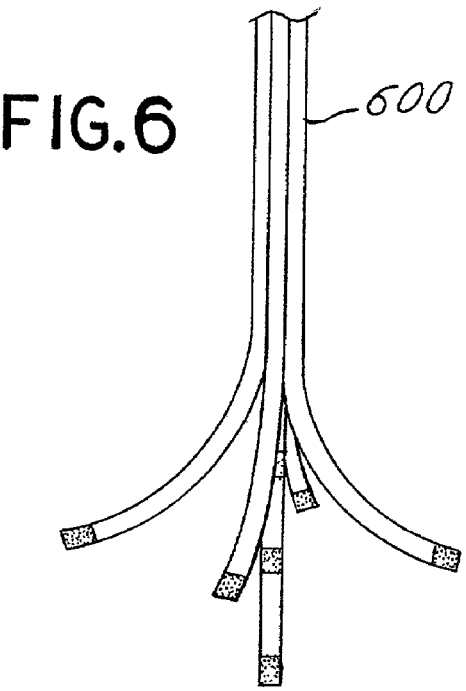
Figure 6A:
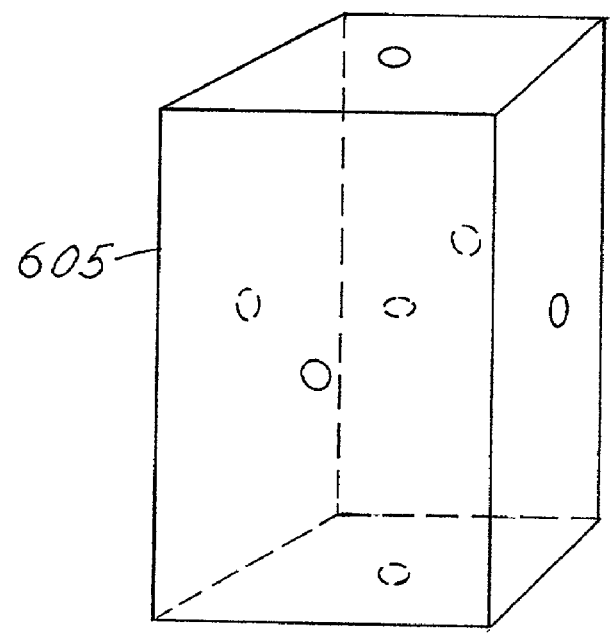
Figure 7:
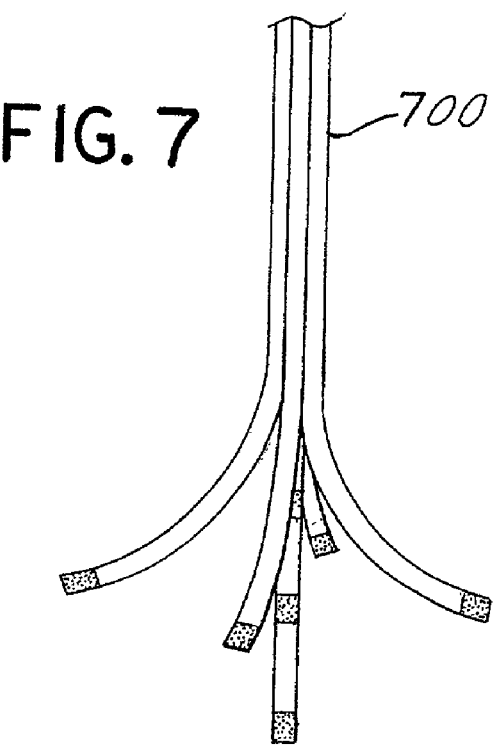
Figure 7A:
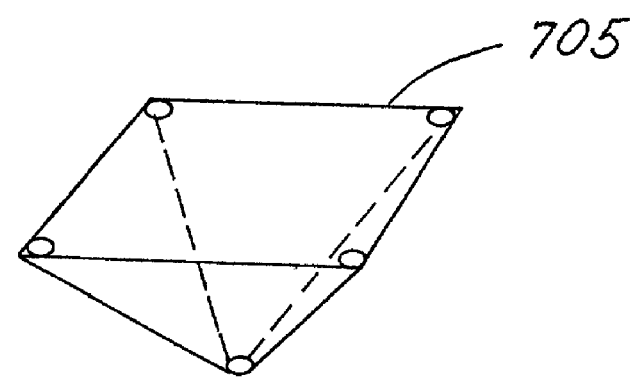
Figure 11:
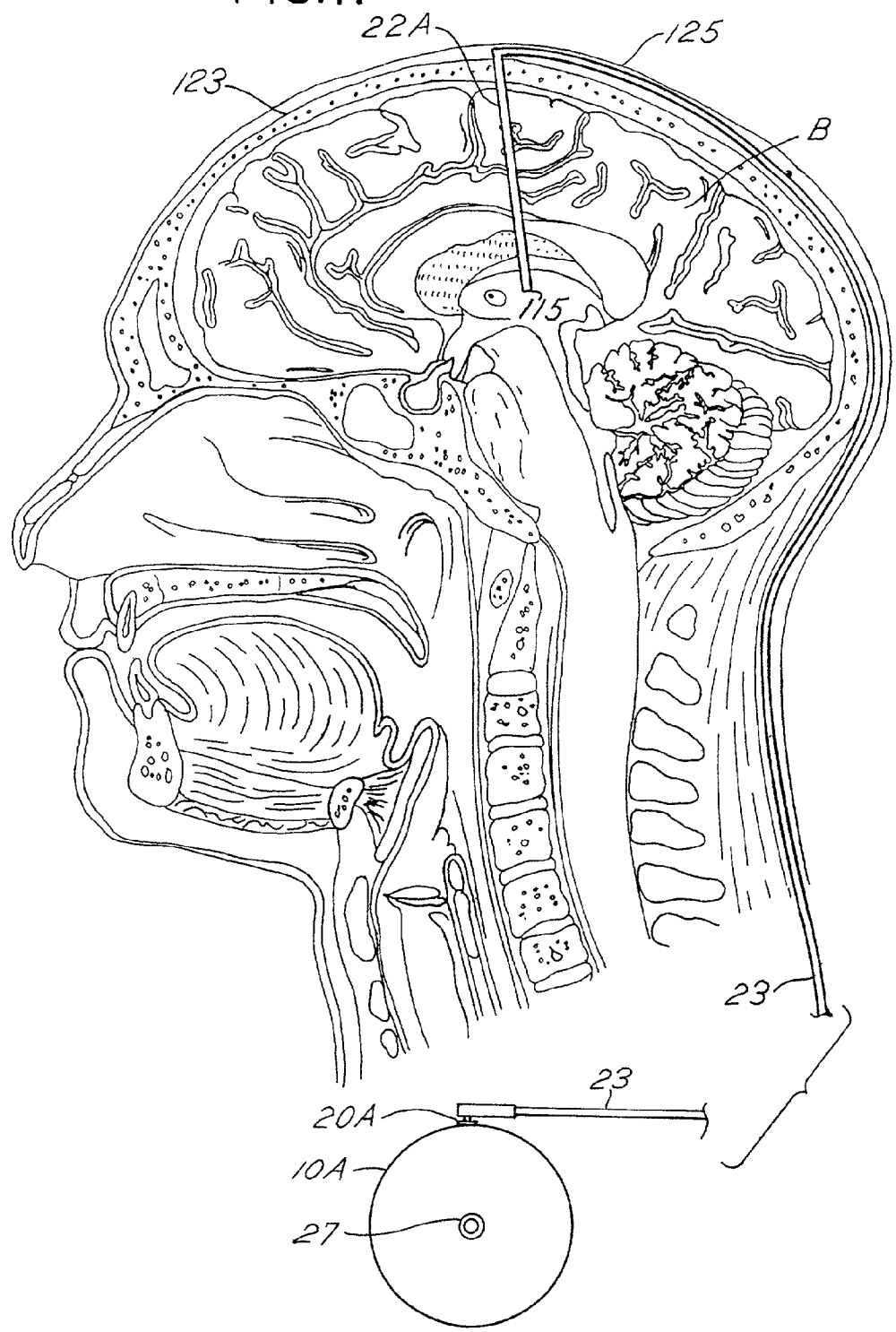
FIG. 11 is an illustration of another embodiment of the present invention wherein one or more drugs are delivered.

In accordance with the present invention, a volume of neural tissue may be stimulated by placement of electrical leads in a non-linear configuration. FIGS. 4-7 illustrate various electrical lead configurations capable of selectively stimulating a volume of neural tissue. Lead 400 of FIG. 4 includes six electrodes at its distal end defining the sides of a cube 405 as shown in FIG. 4A. Cube 405 roughly represents the volume of brain parenchyma that electrodes may potentially stimulate. The subset of tissue actually stimulated is determined by the selection of the particular electrodes to pulse and the pulsing parameters. Lead 400 is preferably five separate leads bundled together. The center lead 401 may be advanced beyond the distal ends of the four outer leads 402 forming the outer surface of cube 405. In this embodiment, the inner lead may also be extended a variable distance from the distal tip of the outer tube. As an example, lead 400 of FIG. 5 shows the situation when five (5) electrodes at its distal end are positioned in a planar configuration as shown in FIG. 5A. This is accomplished by advancing inner lead 401 only as far as needed to position the most distal electrode in the same plane as those curled leads. As illustrated in FIGS. 6, 6A, 7 and 7A those skilled in the art will appreciate that any number of lead and electrode configurations may be possible and still be considered within the spirit and scope of the present invention. For example, another electrode may be on inner lead 401 and positioned right at the point where leads split apart. The lead of the present invention may also provide for drug delivery as shown in FIG. 11 and discussed herein.

Each electrode may be individually connected to signal generator 14 through a conductor in cables 22 which is coupled to signal generator 14 in the manner shown in FIG. 1. Alternatively, each electrode may be coupled to signal generator 14 in a manner disclosed in application Ser. No. 09/024,162 entitled "Living Tissue Stimulation and Recording Techniques with Local Control of Active Sites" and filed Feb. 17, 1998. The electrodes of FIGS. 4-7 may be selectively powered as an anode, cathode or neither. The operator or patient preferably may also selectively adjust the energy, amplitude or pulse parameters delivered to each electrode. The selective control over each electrode may be achieved by signal generator 14 via programmer 20 or a separate controller such as that disclosed in application Ser. No. 09/024,162. Advantageously, the present invention allows the locus of excitation to be selectively adjusted and/or steered to precisely target portions of the brain to achieve the desired treatment therapy. The steering may be accomplished in the manner described in U.S. Pat. No. 5,713,922 which is incorporated herein by reference in its entirety.

FIG. 8 is an illustration of an alternative embodiment of a three dimensional electrode array having a lumen 800 for directing the trajectory of the electrical leads of the present invention. As noted above, the leads can be replaced with catheters. Lumen 800 is permanently introduced into the brain parenchyma to a region roughly in the center of the volume of brain the user wishes to influence. Lumen 800 has a proximal end 805 for accepting one or more leads 815-818A and a distal end 810 having openings 815-818 for directing leads 815A-818A in accordance with a desired trajectory. Ends of leads 815A-818A may produce from openings 815-818 as needed to achieve the desired geometric configuration. It is preferred that leads 815A-818A protrude out from openings 815-818 along a predetermined trajectory. Advantageously, the present invention avoids any slicing movements of the leads 815A-818A while moving outwardly from the central axis of lumen 800 thereby minimizing any risks of damage or bleeding to the brain tissue. Optionally, leads 815A-818A may be made of a silicon material having a predetermined bend or memory along its body to ensure that leads 815A-818A project an opening at the desired angle.

Openings 815-818 preferably direct leads 815A-818A along a predetermined angle and trajectory. FIG. 9 shows a cross-sectional view of cannula 905 along its distal end showing the two openings with curved passageways 916. FIG. 9A illustrates a lead 920 as it is positioned within cannula 905 and lead end 910 is guided out from cannula 905 by opening 915, which includes curved passageway 916. FIG. 10 illustrates the interior portion 905 of a cannula capable of receiving four leads. Interior portion may be inserted within a standard cannula. Those skilled in the art will appreciate that any number of configurations are possible to achieve the desired geometric configurations of the electrodes. Additionally, lead members may contain more than one electrode near their distal end further expanding the geometric options for selectively activating subsections of brain volume.

The present invention is implanted by first implanting cannula 800 so that its distal end 810 is at a predetermined location within the brain. Each lead is then individually inserted within cannula 800 and positioned such that the electrode is at the desired location within the brain.

Figure 12A:
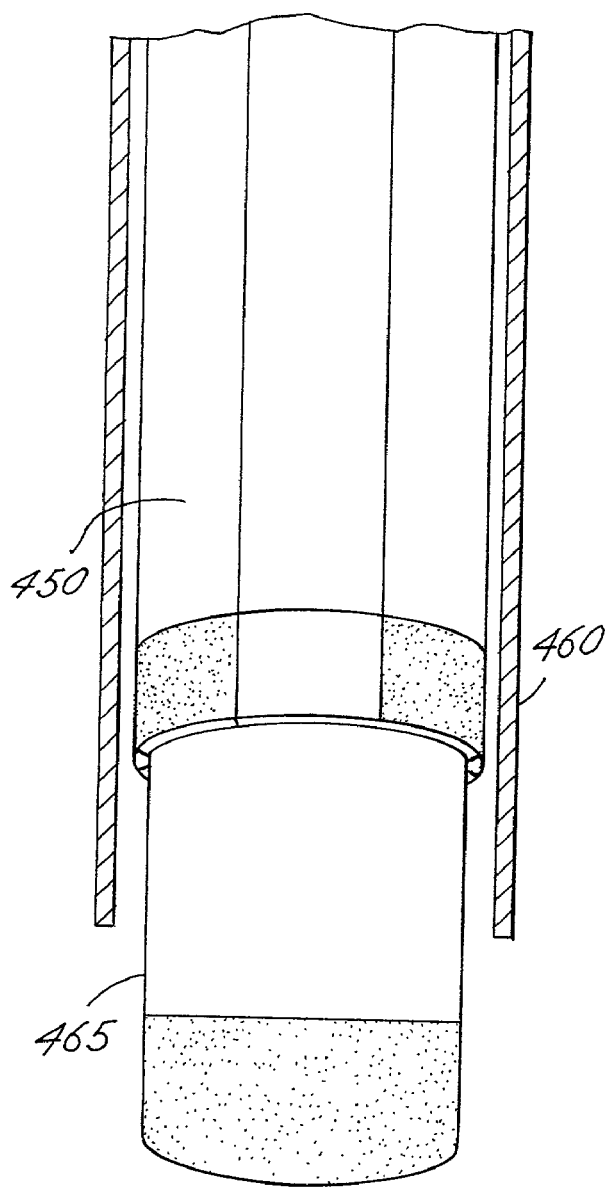
FIGS. 12A-B illustrate another embodiment of the present invention wherein the outer leads are pre-formed so that the distal ends will curl out from the inner lead when unconstrained by an introducing cannula.
Figure 12B:
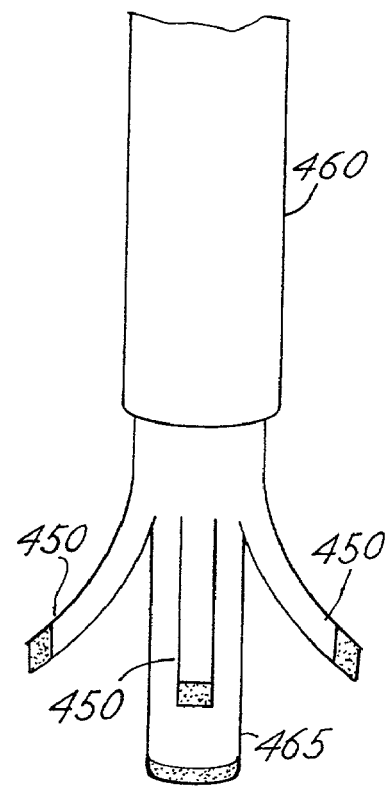

FIG. 12 illustrates another embodiment of the present invention wherein four outer leads 450 are pre-formed so that the distal ends will curl out from the inner lead 465 when unconstrained by an introducing cannula 460. Outer leads 450 and inner lead 465 may be a single lead structure. Cannula 460 may be a standard cannula of a sufficiently large lumen to accept a plurality of leads. Cannula 460 may also be utilized to implant the leads of FIGS. 4-7. Referring back to FIG. 12, lead 450 may be given a predetermined curvature or memory so that the four outer leads 450 curl out when no longer constrained by the inner wall of cannula 460 as shown in FIG. 12A. Again, the outer leads 450 preferably extend out into the brain parenchyma along a predetermined trajectory to minimize injury to brain tissue.

Optionally, the present invention may incorporate a closed-loop feedback system to provide automatic adjustment of the electrical stimulation therapy. The system may incorporate a sensor 130 to provide feedback to provide enhanced results. Sensor 130 can be used with a closed loop feedback system in order to automatically determine the level of electrical stimulation necessary to provide the desired treatment. Sensor 130 may be implanted into a portion of a patient's body suitable for detecting symptoms of the disorder being treated. Sensor 130 is adapted to sense an attribute of the symptom to be controlled or an important related symptom. Sensors suitable for this purpose may include, for example, those disclosed in U.S. Pat. No. 5,711,316 entitled "Method Of Treating Movement Disorders By Brain Infusion" assigned to Medtronic, Inc., which is incorporated herein by reference in its entirety. In cases where the attribute of the symptom is the electrical activity of the brain, stimulating electrodes may be intermittently used to record electrical activity.

Figure 19:
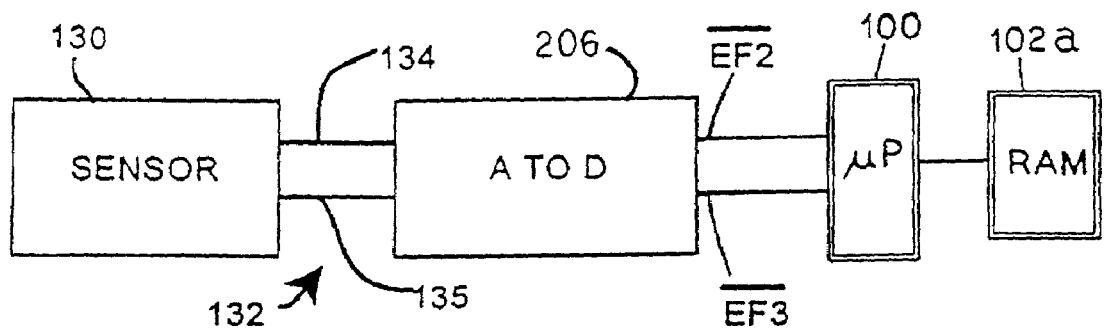
FIG. 19 is a schematic block diagram of a sensor and analog to digital converter circuit used in the preferred embodiment of the invention.
Figure 20:
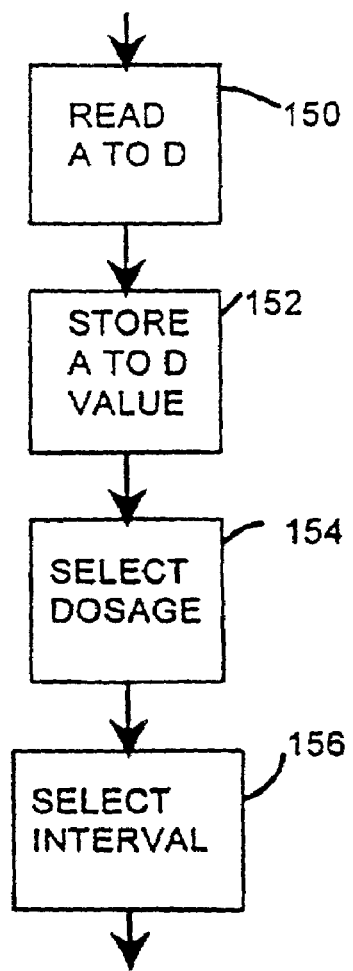
FIG. 20 is a flow chart illustrating a preferred form of a microprocessor program for utilizing the sensor to control the treatment therapy of the brain.

As shown in FIG. 19, the output of sensor 130 is coupled by a cable 132 comprising conductors 134 and 135 to the input of analog to digital converter 206. Alternatively the output of the sensor 130 could communicate through a "body bus" communication system as described in U.S. Pat. No. 5,113,859 (Funke), assigned to Medtronic which is incorporated by reference in its entirety. Alternatively, the output of an external feedback sensor 130 would communicate with the implanted pulse generator 14 or pump 10A through a telemetry down-link. The output of the analog to digital converter 206 is connected to terminals EF2 BAR and EF3 BAR. Such a configuration may be one similar to that shown in U.S. Pat. No. 4,692,147 ("'147 patent") except that before converter 206 is connected to the terminals, the demodulator of the '147 patent (identified by 101) would be disconnected.

Alternatively, one or more electrodes implanted within the brain may serve as a sensor or a recording electrode. When necessary these sensing or recording electrodes may delivery stimulation therapy to the treatment site.

For some types of sensors, a microprocessor and analog to digital converter will not be necessary. The output from sensor 130 can be filtered by an appropriate electronic filter in order to provide a control signal for signal generator 14. An example of such a filter is found in U.S. Pat. No. 5,259,387 "Muscle Artifact Filter, Issued to Victor de Pinto on Nov. 9, 1993, incorporated herein by reference in its entirety.

Figure 13:
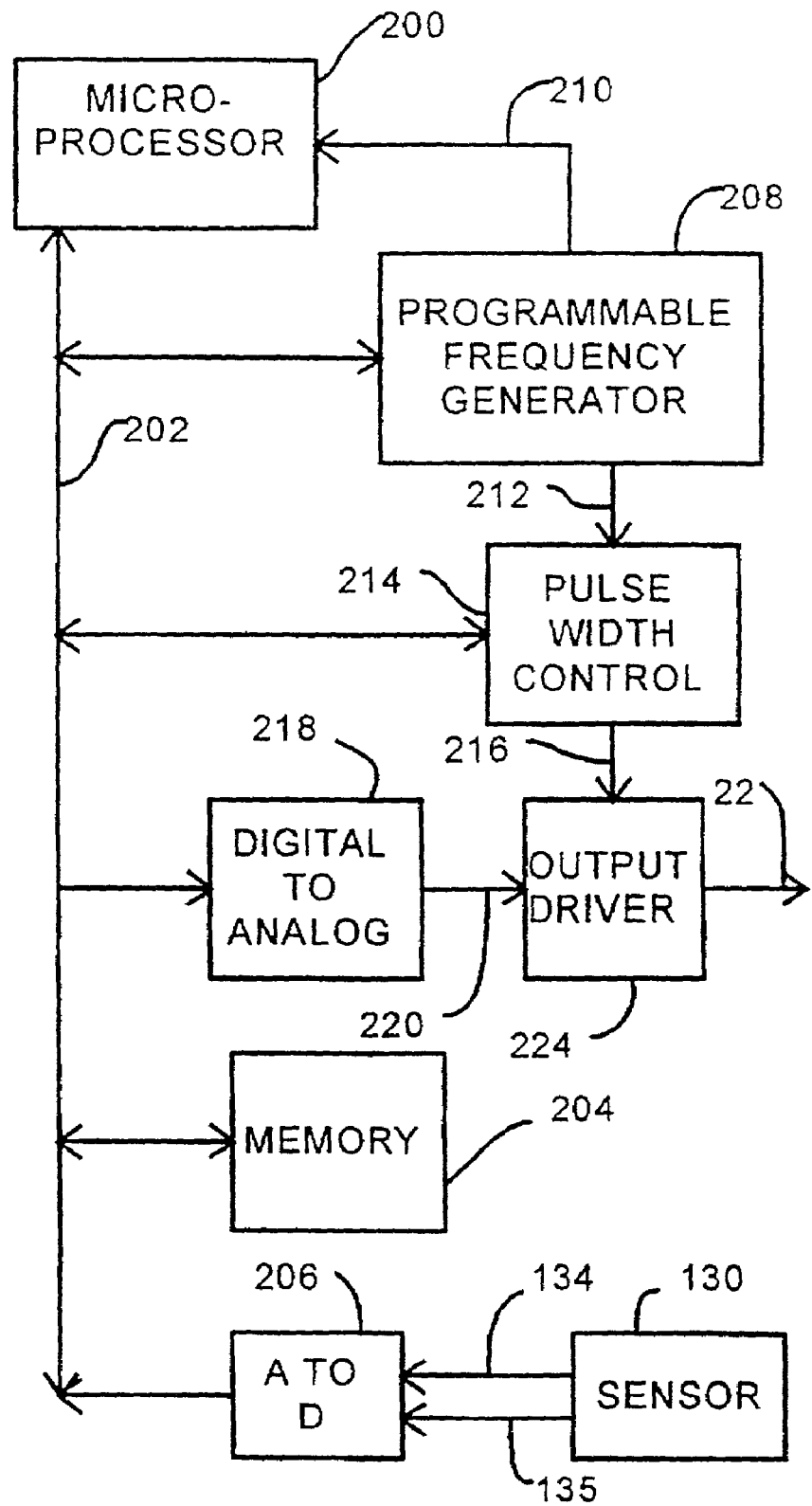
FIG. 13 is a schematic block diagram of a microprocessor and related circuitry used in the preferred embodiment of the invention.

Closed-loop electrical stimulation can be achieved by a modified form of the ITREL II signal generator which is described in FIG. 13. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude. Microprocessor 200 also programs a pulse width control module 214 using bus 202. The pulse width control provides an enabling pulse of duration equal to the pulse width via a conductor . Pulses with the selected characteristics are then delivered from signal generator 14 through cable 22 and lead 22A to the target locations of a brain B. Microprocessor 200 executes an algorithm to provide stimulation with closed loop feedback control as shown in U.S. Pat. No. 5,792,186 entitled "Method and Apparatus of Treating Neurodegenerative Disorders by Electrical Brain Stimulation," and assigned to Medtronic, Inc., which is incorporated herein by reference in its entirety.

Microprocessor 200 executes an algorithm shown in FIGS. 14-18 in order to provide stimulation with closed loop feedback control. At the time the stimulation device 14 is implanted, the clinician programs certain key parameters into the memory of the implanted device via telemetry. These parameters may be updated subsequently as needed. Step 400 in FIG. 14 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which device 14 may use to optimize the therapy. The clinician may also choose the order in which the parameter changes are made (step 400(6)). Alternatively, the clinician may elect to use default values.

Figure 14:
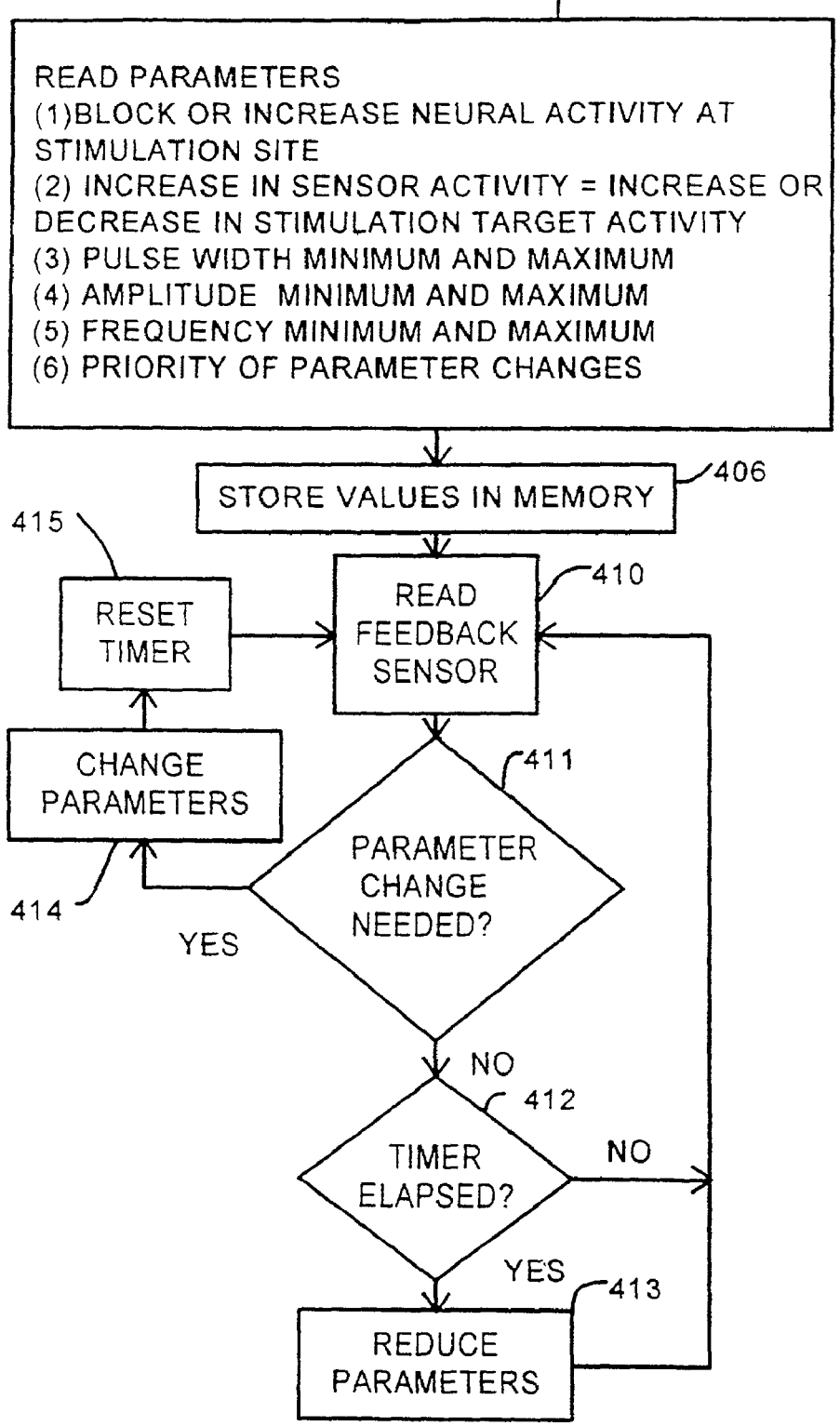
FIGS. 14-18 are flow charts illustrating a preferred form of a microprocessor program for generating stimulation pulses to be administered to the brain.

The algorithm for selecting parameters is different depending on whether the clinician has chosen to block the neural activity at the stimulation target or facilitate the neural activity. FIG. 14 details steps of the algorithm to make parameter changes.

Figure 15:
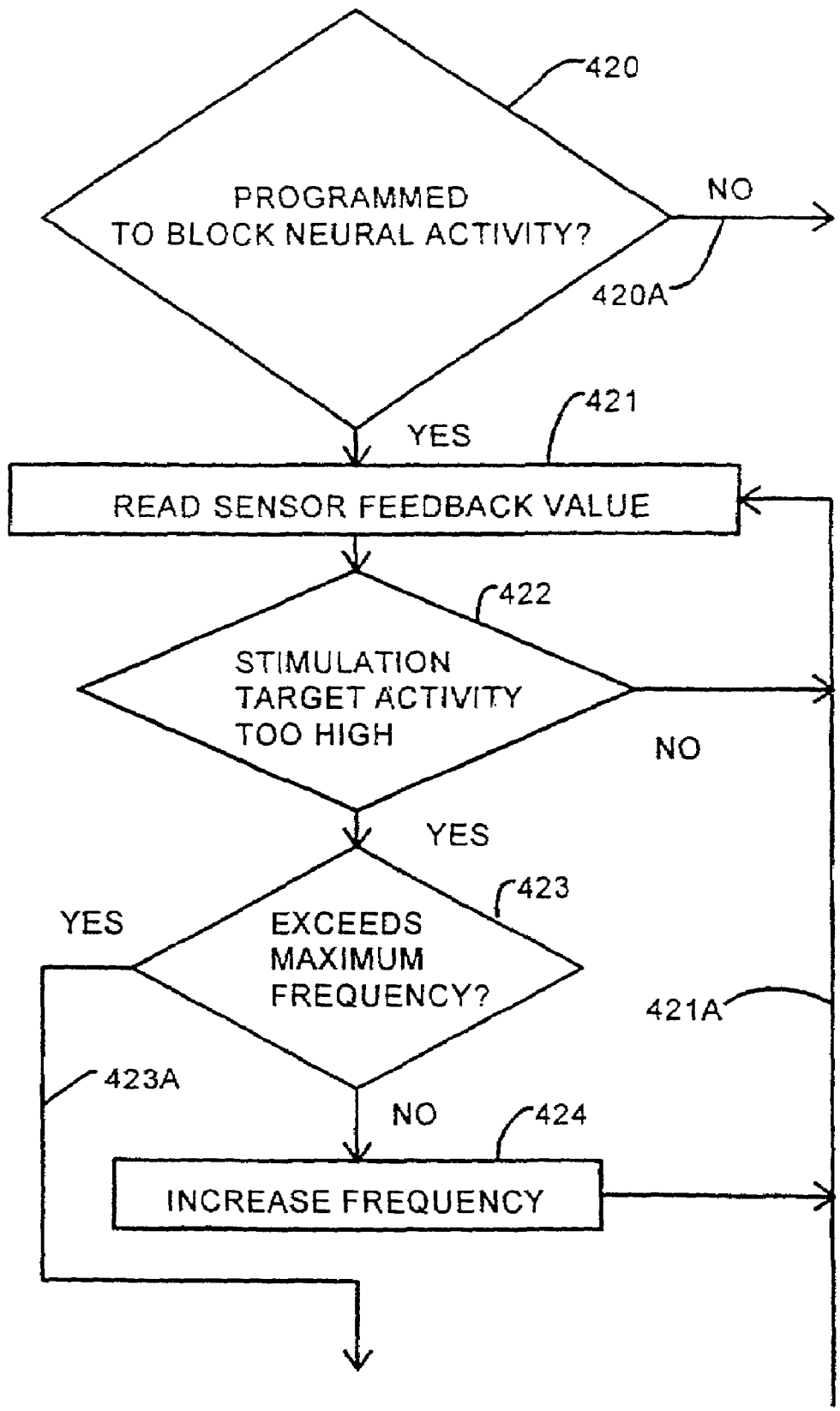
Figure 16:
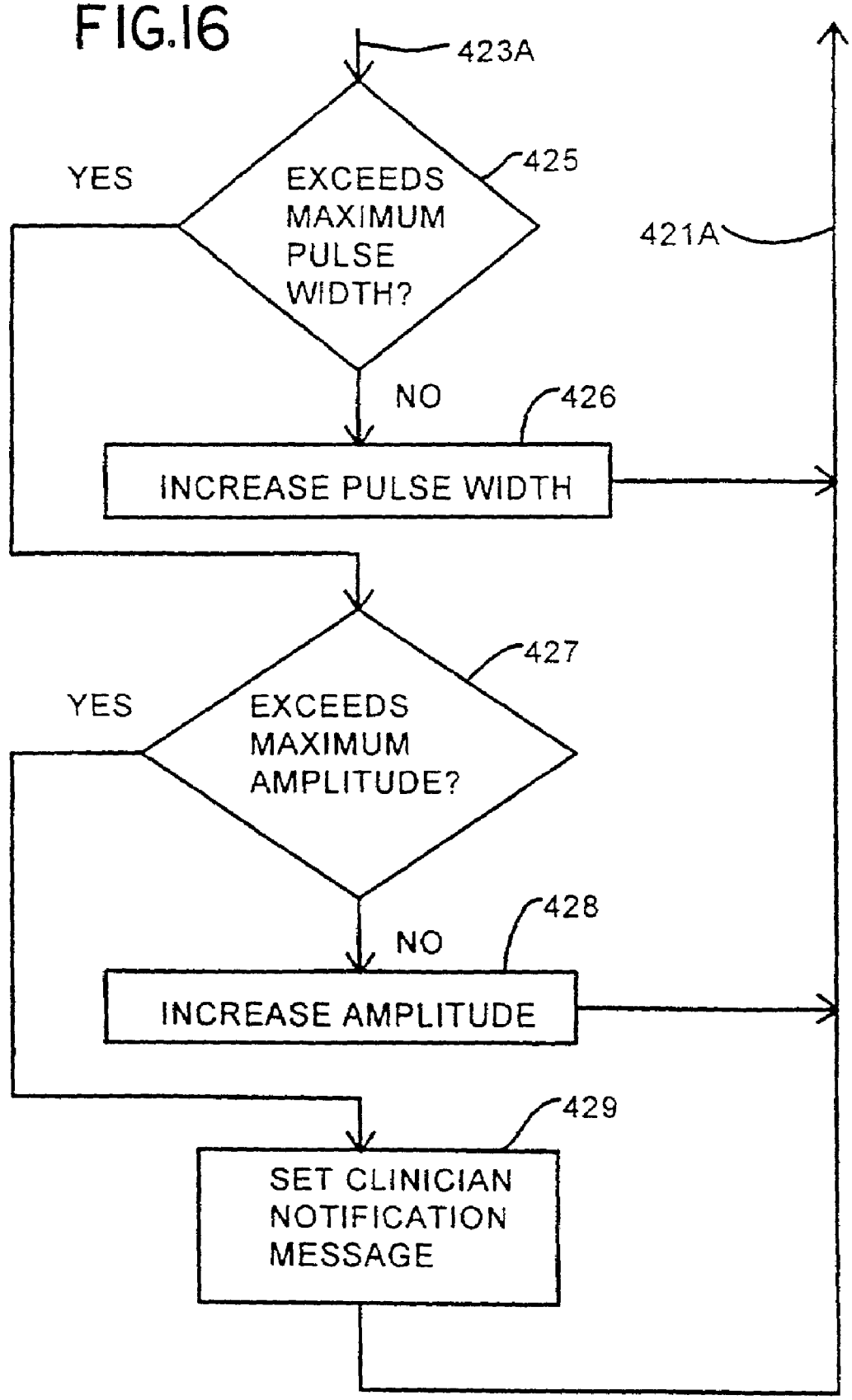
Figure 17:
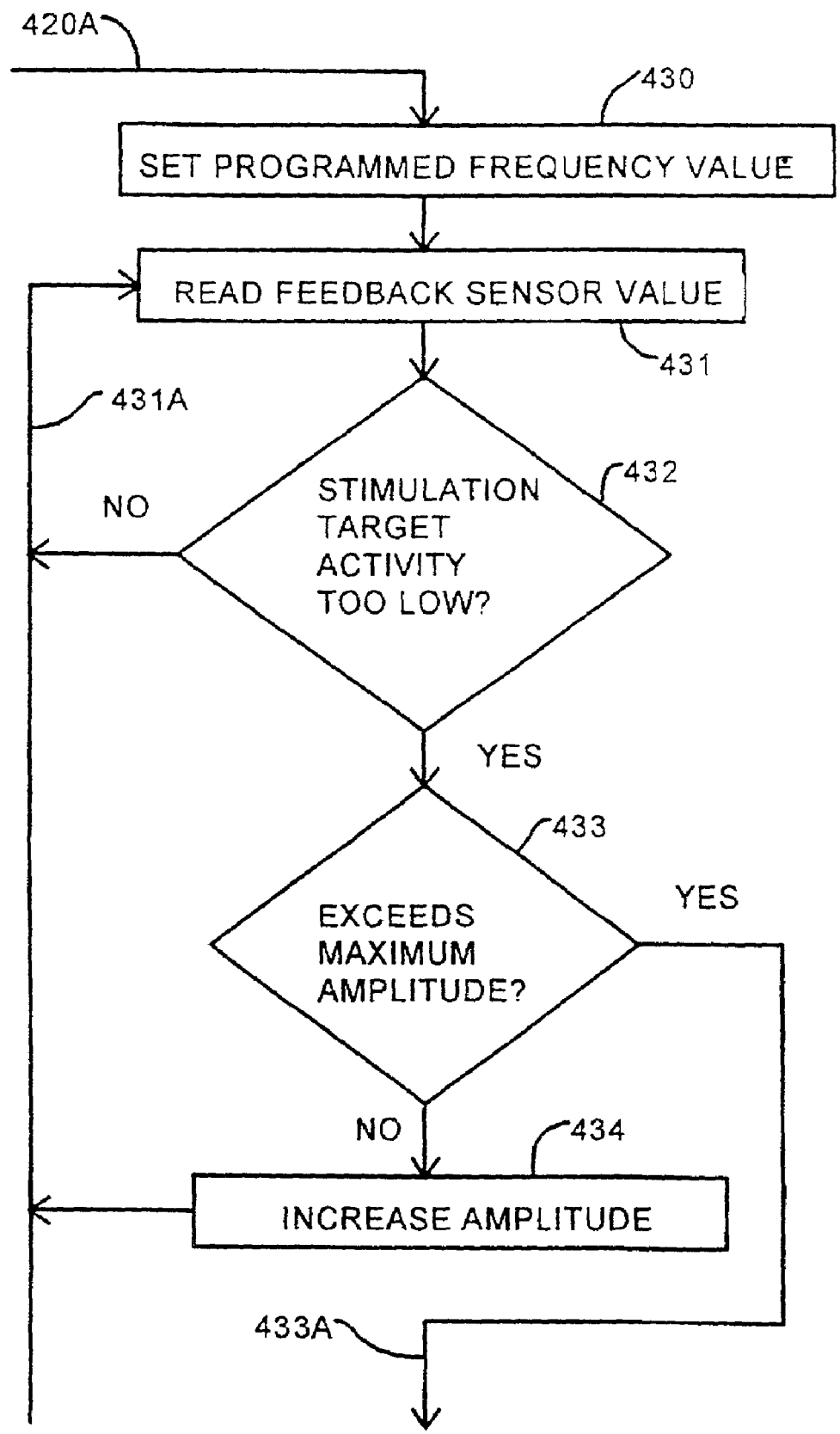

The algorithm uses the clinician programmed indication of whether the neurons at the particular location of the stimulating electrode are to be facilitated or blocked in order to reduce the neural activity in the target nucleus to decide which path of the parameter selection algorithm to follow (step 420, FIG. 15). If the neuronal activity is to be blocked, device 14 first reads the feedback sensor 130 in step 421. If the sensor values indicate the activity in the target neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130. If the frequency parameter is at the maximum, the algorithm next increases the pulse width in step 426 (FIG. 16), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 14 is unable to reduce neural activity to the desired level.

Figure 18:
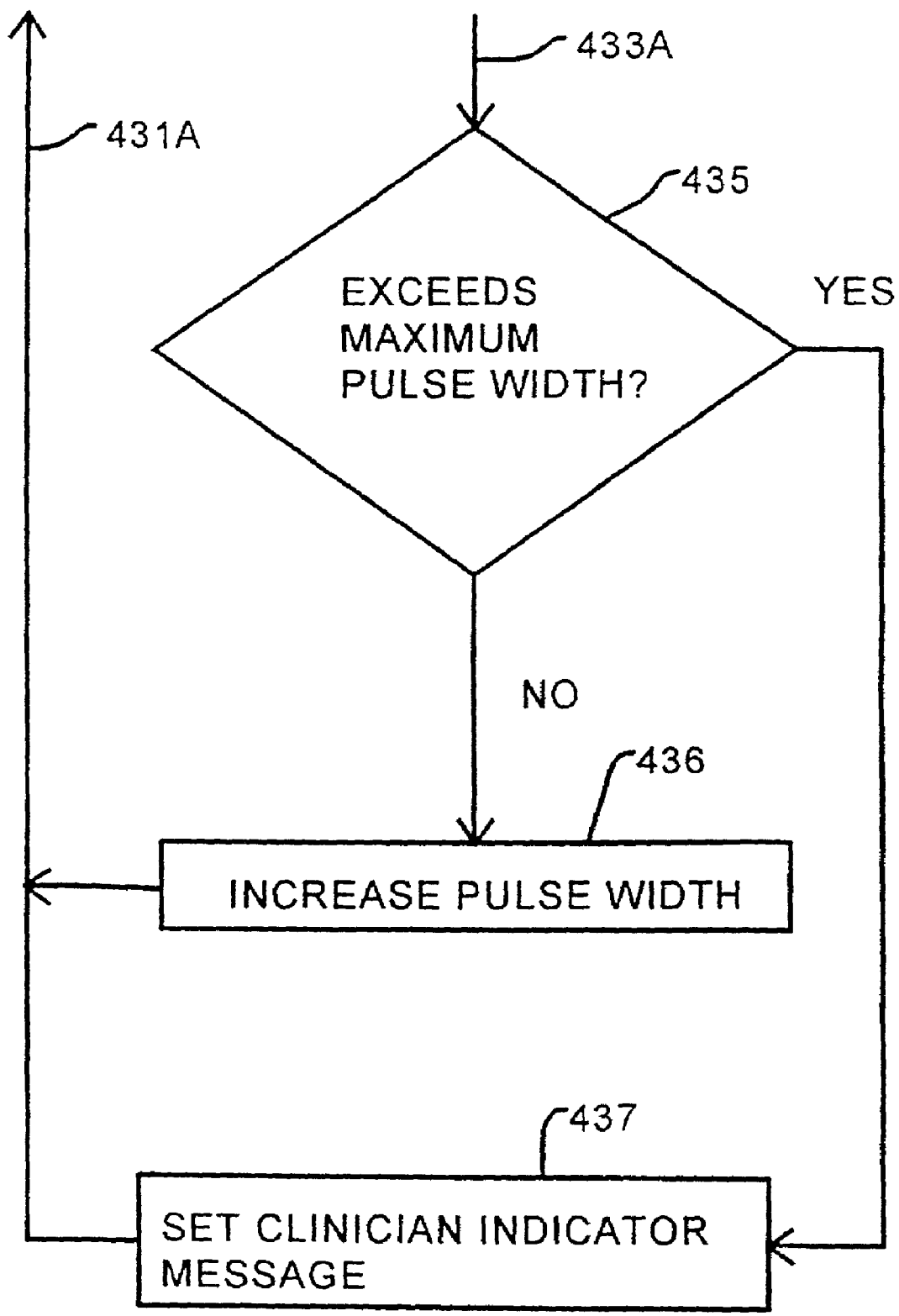

If, on the other hand, the stimulation electrode is placed in a location which the clinician would like to activate in order to increase an inhibition of the target nucleus, the algorithm would follow a different sequence of events. In the preferred embodiment, the frequency parameter would be fixed at a value chosen by the clinician to facilitate neuronal activity in step 430 (FIG. 17) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 18). A lack of adequate reduction of neuronal activity in the target nucleus, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in the target nucleus. Superimposed on the algorithm just described is an additional algorithm to readjust all the parameter levels downward as far as possible. In FIG. 14, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, device 14 tries reducing a parameter in step 413 to determine if control is maintained. If it is, the various parameter values will be ratcheted down until such time as the sensor values again indicate a need to increase them. While the algorithms in FIG. 14 follow the order of parameter selection indicated, other sequences may be programmed by the clinician.

The features and advantages of the present invention for steering an electric field within a brain, a spinal cord, or a peripheral nerve may be implemented in numerous applications. It is generally desirable to excite particular neural tissue elements of the brain to provide a certain treatment such as treatment of a neurological disorder, the relief of chronic pain or to control movements. Often, nearby groups of neurons or axons, e.g., the optic nerve, internal capsule, or medial lemniscus, are in special orientations and groupings. It may be advantageous to avoid affecting them (e.g., preventing stimulation of the perception of the flashes of light) or deliberately to affect them (e.g., excite or inhibit axons of passage). Advantageously, the present invention allows steering of the electrical filed in two- or three-dimensional space such that the precise location and orientation of the electrodes is less critical.

Closed-loop feedback control may also be implemented to steer the electric field to more precisely affect the desired treatment vollume of neural tissue.

Referring back to FIG. 11, the present invention may also be implemented within a drug delivery system. In this embodiment, the therapy delivery device is a pump 10A and the therapy delivery element is a catheter 23. A therapy deliver device or pump 10A made in accordance with the preferred embodiment may be implanted below the skin of a patient. The device has a port 27 into which a hypodermic needle can be inserted through the skin to inject a quantity of a liquid agent, such as a medication or drug. The liquid agent is delivered from the pump 10A through a catheter port 20A into a therapy delivery element or a catheter 23. Catheter 23 is positioned to deliver the agent to specific infusion sites in a brain (B). Pump 10A may take the form of the device numbered 10 that is shown in U.S. Pat. No. 4,692,147 (Duggan), assigned to Medtronic, Inc., Minneapolis, Minn., which is incorporated by reference in its entirety. Settings of the pump 10A such as frequency of delivery of medication and amount of medication to be delivered, can be adjusted to obtain the intended effect.

The distal end of catheter 23 terminates in a cylindrical hollow tube 23A having a distal end 115 implanted into a portion of the brain B by conventional stereotactic surgical techniques. Tube 23A is surgically implanted through a hole in the skull 123. Catheter 23 is joined to pump 10A in the manner shown.

The present invention may be used to deliver treatment therapy to any number of sites in the brain. Particular sites within the brain include, for example, the subthalamic nucleus (STN), the peduncular pontine nucleus (PPN), the caudate or putamen, the internal and external pallidum, the cingulum, the anterior limb of the internal capsule, the anterior nucleus (AN), the centremedian (CM), the dorsal medial nucleus and other nuclei of the thalamus, the hippocampus and other structures in the temporal lobe, the hypothalamus and other structures of the diencephalon, the pons, the medulla, the corext, the cerebellum, the lateral geniculate body, and the medial geniculate body. The desired configuration of the electrodes would depend upon the structure of the portion of the brain to be stimulated or infused and the angle of introduction of the deep brain cannula.

Further, lamina for visual fields are found in the lateral geniculate body, and lamina for tones for hearing are found in the medial geniculate body. Hence, steering of excitation or inhibition by use of this invention can be most useful.

Figure 21:
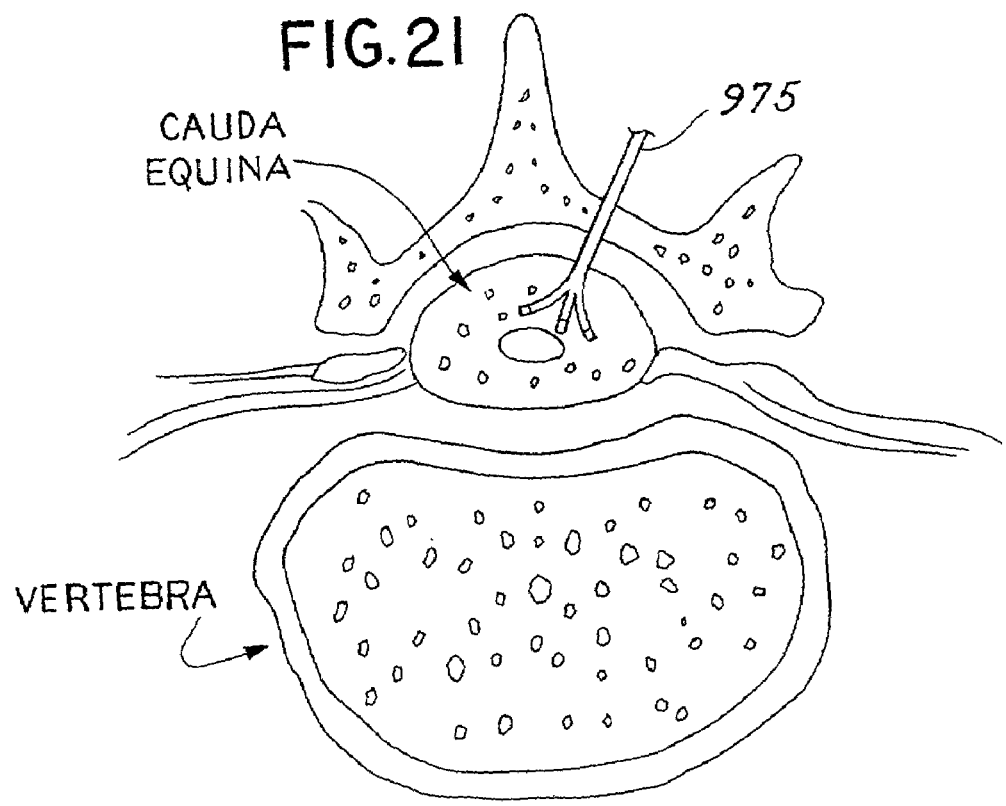
FIG. 21 is a cross-sectional view of the present invention implanted subdurally within the cerebral spinal fluid.
Figure 22:
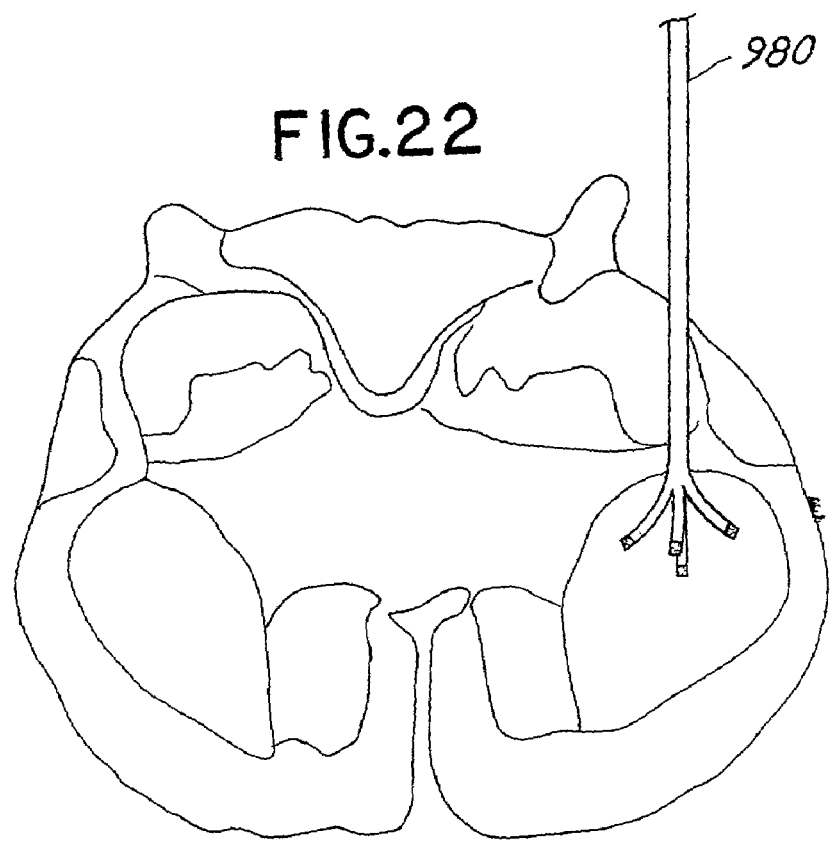
FIG. 22 is a cross-sectional view of the present invention implanted subdurally within spinal cord parenchyma.

Leads of the present invention may also be placed into the parenchyma of the spinal cord. For example, an electrode array may be located in the region of a specified spinal cord segment where neural tissue related to the bladder may be influenced. Selective activation of regions of the ventral horn of the spinal cord in these spinal segments may enable selective activation of specific actions related to bladder function. Alternatively, placement of leads in the region of the connus medullaris (FIG. 22) or cauda equina (FIG. 21) may further enhance the ability to selectively activate element of urinary bladder control. Leads 975 or 980 of FIG. 21 or 22 may be implanted under known techniques for implanting leads within the spinal cord.

Figure 23:
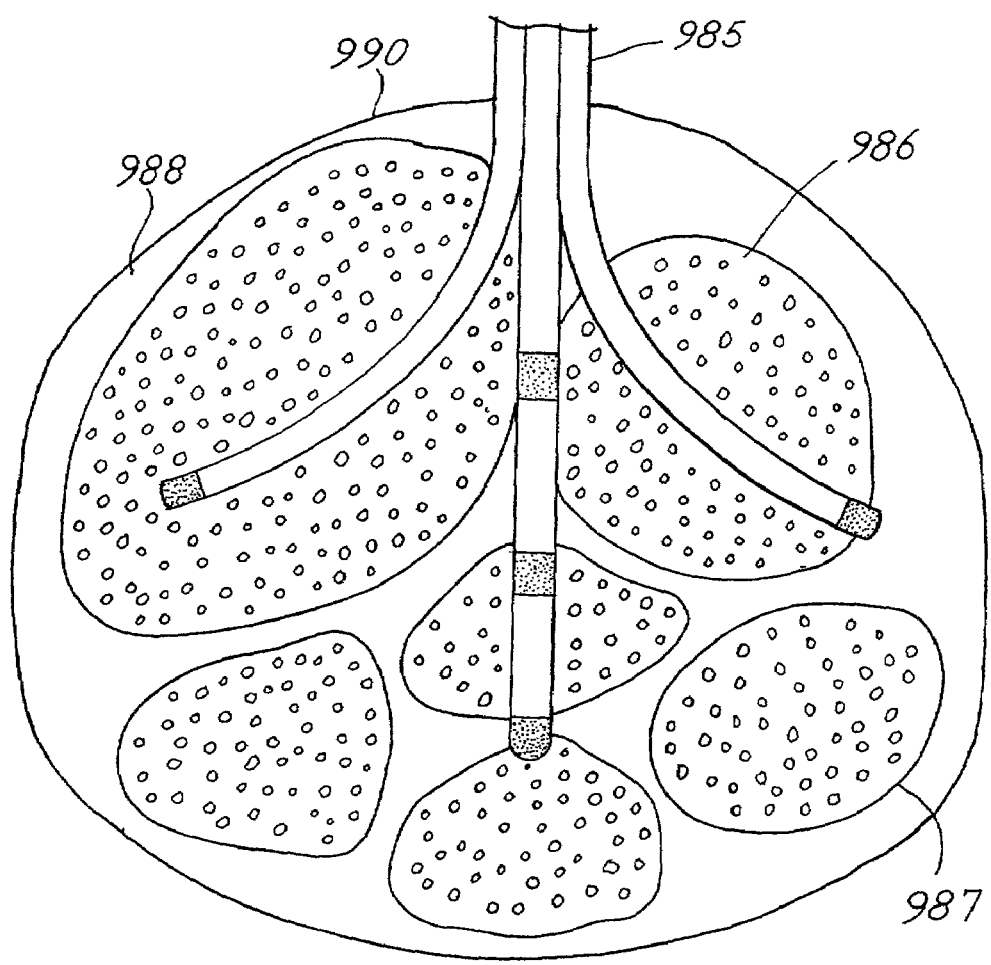
FIG. 23 is a cross-sectional view of the present invention implanted within a peripheral nerve.

As shown in FIG. 23, leads of the present invention may also be placed in a peripheral nerve to provide selective activation of individual nerve fascicles or neurons each innervating a different body region or subserving a different physiological function. Selective activation individual nerve fascicles or neurons may allow discrimination of regions of body surface when evoking paresthesia activation to treat chronic pain. Alternatively, such an embodiment would allow selective activation of different muscle groups when performing functional electrical stimulation.

Advantageously, the present invention may be used to selectively steer and control the stimulation of neurons or neural tissue to deliver a desired treatment therapy. Those skilled in that art will recognize that the preferred embodiments may be altered or amended without departing from the true spirit and scope of the invention, as defined in the accompanying claims. For example, the present invention may also be implemented within a drug delivery system where the leads are implanted within the brain in accordance with the present invention to provide electrical stimulation as well as delivery of one or more drugs.

We claim:

1. An implantable agent delivery system for providing treatment therapy to a volume of neural tissue comprising in combination:

a cannula having a central lumen distal end with a plurality of openings provided near the lumen distal end, each opening capable of directing a catheter outwardly along a distinct predetermined trajectory, at least one of the openings having a curved passageway defined by an inner curve and an outer curve, the inner curve and the outer curve having substantially the same shape so as to direct a catheter away from the central axis of the cannula along the predetermined trajectory, wherein, in operation, slicing caused by installation of the catheter may be substantially avoided;

a first catheter and a second catheter that are insertable within the cannula, wherein the first catheter protrudes through a first opening of the cannula and the second catheter protrudes through a second opening of the cannula, wherein each catheter is positioned to deliver a liquid agent, and wherein the liquid agent has a desired effect in providing the treatment therapy; and a therapy delivery device that stores the liquid agent and couples to the first catheter and the second catheter to deliver the liquid agent, wherein the cannula, the first and second catheter and the therapy delivery device are each configured to be completely implantable under a skin of a patient.

2. The agent delivery system of claim 1, wherein the therapy delivery device comprises a replenishment port, and wherein additional liquid agent is inserted into the therapy delivery device through the replenishment port.

3. The agent delivery system of claim 2, wherein the additional liquid agent is injected with a hypodermic needle through the replenishment port.

4. The agent delivery system of claim 1, further comprising:
a first sensor that generates a first signal that is indicative of a condition to be treated; and
a processor that is coupled to the first sensor, that receives the first signal from the first sensor, and that causes the first catheter and the second catheter to deliver the liquid agent at a desired rate, wherein the first sensor and the processor are each configured to be completely implanted under the skin of the patient.

5. The agent delivery system of claim 4, wherein the therapy delivery device comprises a pump, and wherein the processor is coupled to the pump to provide the desired rate of infusing the liquid agent through said each catheter.

6. The agent delivery system of claim 4, wherein the processor is configured to perform:
(a) reading at least one parameter that is associated with the treatment therapy;
(b) obtaining a level of the first signal; and
(c) determining a desired rate of infusing the liquid agent through the first catheter and the second catheter according to the level of the first signal and the at least one parameter.

7. The agent delivery system of claim 6, wherein the processor is further configured to perform:
(d) adjusting the at least one parameter in response to the level of the first signal.

8. The agent delivery system of claim 7, wherein (d) comprises:
(1) if a timer has expired and if the at least one parameter has not changed during a corresponding time interval, reducing the at least one parameter.

9. The agent delivery system of claim 7, wherein (d) comprises:
(1) changing the at least one parameter in response to the level of the first signal; and
(2) resetting a timer to restart a corresponding time interval.

10. The agent delivery system of claim 6, wherein (c) comprises:
(1) if the agent delivery system is programmed to block neural activity, determining whether a target activity is excessive in accordance with the level of the first signal; and
(2) in response to (1), increasing at least one setting that is associated with the desired rate of infusing the liquid agent, wherein the at least one setting does not exceed a maximum value.

11. The agent delivery system of claim 10, wherein (c) further comprises:
(3) if the increasing in (2) would cause the at least one setting to exceeds the maximum value, providing an indicative output.

12. The agent delivery system of claim 6, wherein (c) comprises:
(1) if the agent delivery system is programmed to increase neural activity, determining whether a target activity is not sufficient in accordance with the level of the first signal; and
(2) in response to (1), increasing at least one setting that is associated with the desired rate of infusing the liquid agent, wherein the at least one setting does not exceed a maximum value.

13. The agent delivery system of claim 12, wherein (c) further comprises:
(3) if the increasing in (2) would cause the at least one setting to exceed the maximum value, providing an indicative output.

14. The agent delivery system of claim 4 further comprising a second sensor that generates a second signal that is indicative of the condition to be treated, and wherein the processor receives the second signal, and wherein the processor causes the first catheter and the second catheter to deliver the liquid agent in accordance with levels of the first signal and second signal.

15. The agent delivery system of claim 4, further comprising:
an interface that is connected to the processor, wherein the interface is configured to be completely implanted below the skin of the patient; and
a programmer that communicates to the processor through the interface to configure the processor in accordance with the therapy treatment.

16. The agent delivery system of claim 15, wherein the programmer communicates to the processor over a telemetry communications link.

17. The agent delivery system of claim 1, wherein the therapy delivery device is coupled to a first and a second catheter, wherein the delivery system is configured to deliver at least two drugs through the first and second catheters.

18. The agent delivery system of claim 1, wherein the treatment therapy is for a neurological disorder.

19. The agent delivery system of claim 1, wherein the liquid agent is selected from the group consisting of a medication and a drug.

20. An implantable drug delivery system that provides treatment therapy for a nervous system disorder to a volume of neural tissue comprising in combination:
a cannula having a lumen distal end with a plurality of openings provided near the lumen distal end, each opening capable of directing a catheter outwardly along a distinct predetermined trajectory, at least one of the openings having a curved passageway defined by an inner curve and an outer curve, the inner curve and the outer curve having substantially the same shape, so as to direct a catheter away from the central axis of the cannula along the predetermined trajectory, wherein, in operation, slicing caused by installation of the catheter may be substantially avoided;
a first catheter and a second catheter that are insertable within the cannula, wherein the first catheter protrudes through a first opening of the cannula and the second catheter protrudes through a second opening of the cannula, wherein each catheter is positioned to deliver a drug, and wherein the drug has a desired effect in providing the treatment therapy;
a pump that stores the drug and couples to the first catheter through a first catheter port and the second catheter through a second catheter port to deliver the drug at a desired rate;
a sensor that generates a signal that is indicative of a condition to be treated; and
a processor that is coupled to the sensor in order to receive the signal from the sensor and that instructs the pump to infuse the drug at the desired rate through the first catheter and the second catheter, wherein the cannula, the first and second catheter, the pump, the sensor and the processor are each configured to be completely implantable under a skin of a patient.

21. An implantable agent delivery system for providing treatment therapy to a volume of neural tissue comprising in combination:
- a cannula having a lumen distal end with a plurality of openings provided near the lumen distal end, each opening capable of directing a catheter outwardly along a distinct predetermined trajectory, at least one of the openings having a curved passageway defined by an inner curve and an outer curve, the inner curve and the outer curve having substantially the same shape, so as to direct a catheter away from the central axis of the cannula along the predetermined trajectory, wherein, in operation, slicing caused by installation of the catheter may be substantially avoided;
- a first catheter and a second catheter that are insertable within the cannula, wherein the first catheter protrudes through a first opening of the cannula and the second catheter protrudes through a second opening of the cannula, wherein each catheter is positioned to deliver a liquid agent; and
- a therapy delivery device that stores the liquid agent and couples to the first catheter and the second catheter to deliver the liquid agent, wherein the cannula, the first and second catheter and the therapy delivery device are each configured to be completely implantable under a skin of a patient.

22. The agent delivery system of claim 21, wherein the first catheter is configured to deliver the liquid agent to a first position and the second catheter is configured to deliver the liquid agent to a second position, the agent delivery system further comprising:
- a sensor that generates a signal, the sensor being located in a proximity of one of the positions; and
- a processor that is coupled to the first sensor, that receives the signal from the sensor, and that causes the first catheter and the second catheter to deliver the liquid agent in accordance with the signal, wherein the sensor and the processor are each configured to be completely implanted under the skin of the patient.

23. The agent delivery system of claim 22, further comprising:
- an interface that is connected to the processor, wherein the interface is configured to be completely implanted under the skin of the patient; and
- an external programmer that communicates to the processor through the interface to configure the processor in accordance with the therapy treatment.

24. An agent delivery system of claim 21, wherein the therapy delivery has a port, and wherein additional liquid agent is inserted into the therapy delivery device through the port.

25. The agent delivery system of claim 21, wherein the treatment therapy is for a neurological disorder.

* * * * *

UNITED STATES PATENT AND TRADEMARK OFFICE
CERTIFICATE OF CORRECTION

PATENT NO. : 7,442,183 B2  Page 1 of 1
APPLICATION NO. : 10/053329
DATED : October 28, 2008
INVENTOR(S) : Michael Baudino et al.

It is certified that error appears in the above-identified patent and that said Letters Patent is hereby corrected as shown below:

<u>Column 11</u>
Line 60, "to exceeds the" should read -- to exceed the --.

Signed and Sealed this

Twenty-eighth Day of July, 2009

JOHN DOLL
*Acting Director of the United States Patent and Trademark Office*